US00PP26080P3

(12) United States Plant Patent
Klemm et al.

(10) Patent No.: US PP26,080 P3
(45) Date of Patent: Nov. 10, 2015

(54) ***SUTERA* PLANT NAMED 'KLESG13255'**

(50) Latin Name: *Sutera grandiflora*
Varietal Denomination: KLESG13255

(71) Applicant: Klemm+Sohn GmbH & Co. KG, Stuttgart (DE)

(72) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 119 days.

(21) Appl. No.: 13/987,190

(22) Filed: Jul. 9, 2013

(65) Prior Publication Data

US 2015/0020282 P1 Jan. 15, 2015

(51) Int. Cl.
*A01H 5/00* (2006.01)

(52) U.S. Cl.
USPC ..... Plt./485

(58) Field of Classification Search
USPC ..... Plt./485
CPC ..... A01H 5/00
See application file for complete search history.

(56) References Cited

PUBLICATIONS

Ball Horticultural Company 2013.*

* cited by examiner

*Primary Examiner* — Keith O. Robinson
(74) *Attorney, Agent, or Firm* — James M. Weatherly; Bethany Reid Roahrig; Cochran Freund & Young, LLC

(57) ABSTRACT

A new *Sutera* plant particularly distinguished by having a white flower color, large flowers and more branching, is disclosed.

1 Drawing Sheet

Genus and species: *Sutera grandiflora.*
Variety denomination: 'KLESG13255'.

BACKGROUND OF THE NEW PLANT

The present invention comprises a new and distinct variety of *Sutera,* botanically known as *Sutera grandiflora*, and hereinafter referred to by the variety name 'KLESG13255'. 'KLESG13255' originated from an open-pollination between the proprietary female *Sutera* variety 'G Lavender' (unpatented) and an unknown male *Sutera* variety.

In August of 2009, seed was collected from the open-pollination cross of two *Sutera* parental lines, 'G Lavender' and an unknown *Sutera* in Stuttgart, Germany. The seeds were sown and plants were grown for evaluation. A plant line was selected in May 2010, which had a white flower color and subsequently named 'KLESG13255'. In May 2010, 'KLESG13255' was first vegetatively propagated by in-vitro cultivation in Stuttgart, Germany. 'KLESG13255' was found to reproduce true to type in successive generations of asexual propagation via in-vitro cultivation in Stuttgart, Germany.

CROSS REFERENCE TO RELATED APPLICATIONS

Plant Breeder's Rights for 'KLESG13255' were applied for in Canada on Feb. 8, 2013, Application No. 13-7928. 'KLESG13255' has not been made publicly available or sold more than one year prior to the filing date of this application.

SUMMARY

The following are the most outstanding and distinguishing characteristics of this new variety when grown under normal horticultural practices in Stuttgart, Germany.

1. White flower color;
2. Large flowers; and
3. More branching.

DESCRIPTION OF THE PHOTOGRAPH

This new *Sutera* plant is illustrated by the accompanying photograph which shows a close-up of the flowers.

The photograph is of a 10-week-old plant grown in a controlled greenhouse environment in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLESG13255'. The data which define these characteristics were collected from asexual reproductions by in-vitro cultivation carried out in Stuttgart, Germany. Data was collected on 11-week-old plants grown in a controlled greenhouse environment in Stuttgart, Germany in May 2013. Color references are to The R.H.S. Colour Chart of The Royal Horticultural Society of London (R.H.S.), (2005).

Classification:
*Family.*—Scrophulariaceae.
*Botanical.—Sutera grandiflora.*
*Common.—Sutera.*
*Designation.*—'KLESG13255'.

Parentage:

*Female parent.*—Proprietary *Sutera* line 'G Lavender' (unpatented).

*Male parent.*—An unknown *Sutera* line.

Plant:

*Habit.*—Trailing.

*Height.*—About 9.0 cm.

*Spread.*—37.0 cm.

*Life cycle.*—Blooms from April until September.

*Form.*—Round.

*Time to produce a rooted cutting.*—4 weeks.

*Time to bloom from propagation.*—5 weeks.

*Lastingness of inflorescence on the plant.*—About 7 days.

*Rooting habit and color.*—Fine, fibrous roots; color is white to cream-white.

Stems:

*Number of stems per plant.*—9.

*Length.*—About 23.0 cm.

*Diameter.*—0.8 cm.

*Internode length.*—About 1.5 cm.

*Color.*—RHS 144A.

*Texture.*—Smooth.

*Anthocyanin.*—Absent.

Leaves:

*Arrangement.*—Single, opposite.

*Average number of leaves per branch.*—About 20, and dependent on the age of the plant.

*Leaf type.*—Simple.

*Leaf variegation.*—Absent.

*Shape.*—Ovate, acute angle to the stem.

*Apex.*—Acute.

*Base.*—Cordate.

*Margin.*—Serrate.

*Length.*—Between 1.6 cm to 2.5 cm.

*Width.*—Between 1.8 cm and 3.0 cm.

*Color.*—Immature and mature leaves: Upper surface: RHS 137A. Lower surface: RHS 137C.

*Texture.*—Both upper and lower surfaces: Leathery.

*Venation type.*—Pinnate.

*Venation color.*—Upper and lower surfaces: RHS 144A.

*Fragrance.*—Present.

*Petiole.*—Length: 0.7 cm. Diameter: 0.1 cm. Texture: Pubescence. Color: RHS 138B.

Inflorescence:

*Blooming habit.*—Freely flowering.

*Natural flowering season.*—Flowers 4 weeks after potting; flowers all year round in moderate climates; if in full sun and heat flowering stops.

*Persistent or self-cleaning.*—Flowers are not really self-cleaning but because of the quantity of flowers, old flowers will not be noticeable.

*Peduncle.*—Absent.

*Quantity of inflorescence per stem.*—About 10.

*Type of inflorescence.*—Flowers are often solitary, most often 2 flowers per node are developed.

*Fragrance.*—Present.

Pedicel:

*Color.*—RHS 144A.

*Length.*—1.0 cm to 1.5 cm.

*Diameter.*—About 0.1 cm.

*Texture.*—Pubescent.

*Strength.*—Moderate to strong.

Bud:

*Shape.*—Tubular.

*Diameter.*—About 0.3 cm.

*Length.*—About 0.5 cm.

*Color* (*at tight bud*).—RHS 155A.

Corolla (flower):

*Type and shape.*—Single-type, nearly round, lower part tube and funnel shaped formed by 5 fused petals, upper part is salver shaped formed by the partly free petal lobes.

*Corolla, horizontal diameter.*—About 2.2 cm.

*Corolla, total length.*—About 2.5 cm. Color of throat: Inner surface: RHS 23A. Outer surface: RHS 15B. Diameter: 0.4 cm. Texture: Inner and outer surfaces: Smooth.

*Corolla tube length.*—0.7 cm.

*Corolla tube width.*—0.5 cm.

Petal (lobes):

*Apex.*—Rounded tips.

*Base.*—Fused.

*Margin.*—Entire.

*Color.*—Inner surface: RHS N999D. Outer surface: RHS N999D.

*Texture.*—Upper and lower surfaces: Smooth.

*Length.*—About 1.0 cm.

*Width.*—About 1.2 cm.

Calyx:

*Arrangement and appearance.*—Whorl of 5 sepals surrounding the base of the flower tube, sepals are fused at the base.

*Sepals.*—Color: Upper and lower surfaces: RHS 139C. Length: 1.2 cm. Width: 0.1 cm. Apex: Acute. Base: Fused. Margin: Entire. Texture: Upper and lower surfaces: Densely pubescent. Shape: Lanceolate, acuminate.

Reproductive organs:

*Stamens.*—Quantity: 4. Filament: Color: RHS 155B. Length: 1.1 cm. Diameter: 0.1 cm. Anther color: RHS 15D. Pollen amount: Abundant. Pollen color: RHS 22A.

*Pistil.*—Quantity per flower: 1. Length: 1.3 cm. Stigma color: RHS 145C. Style color: RHS 155B. Style length: 0.7 cm to 1.2 cm. Ovary color: RHS 138B.

Fruit and seed set:

*Capsulates/fruit.*—Color: RHS 137C. Size: 0.5 cm×0.4 cm. Shape: Ovate.

*Seeds.*—Color: RHS 20A. Size: About 0.1 cm. Shape: Round.

Disease and pest/insect resistance: None observed.

COMPARISON WITH PARENTAL LINE AND KNOWN VARIETY

'KLESG13255' is a distinct variety of *Sutera* having a white flower color; 'KLESG13255' is distinguished from its female parent as described in Table 1:

TABLE 1

| Comparison with Parental Line | | |
|---|---|---|
| Trait | Variety 'KLESG13255' | Female parent 'G Lavender' |
| Color of flower | White | Lavender |

'KLESG13255' is most similar to the *Sutera* plant named 'Summer White Falls' (unpatented). Differences between the two varieties are described in Table 2:

TABLE 2

| Comparison with Similar Variety | | |
|---|---|---|
| Trait | Variety 'KLESG13255' | Commercial line 'Summer White Falls' (unpatented) |
| Flower size | Bigger flowers than 'Summer White Falls' | Smaller flowers than 'KLESG13255' |
| Branching | More branching than 'Summer White Falls' | Less branching than 'KLESG13255' |

We claim:

1. A new and distinct variety of *Sutera* plant named 'KLESG13255' as illustrated and described herein.

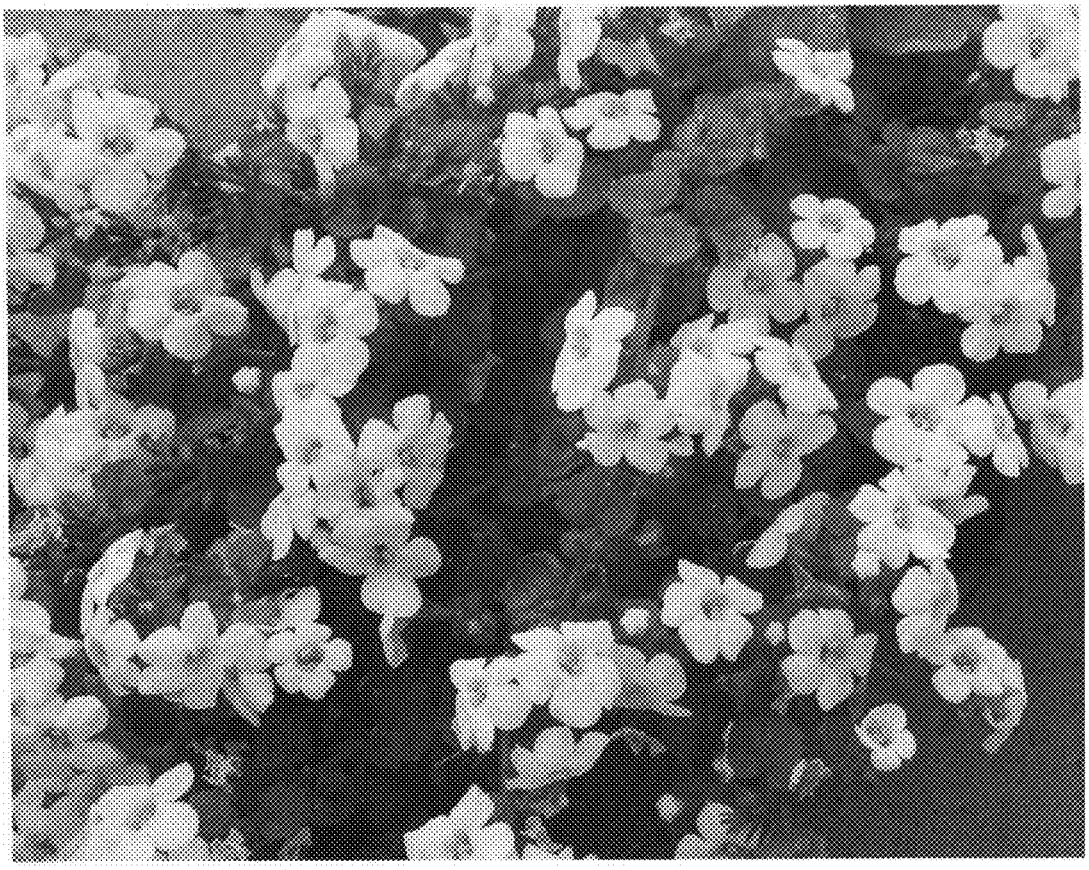

* * * * *